(12) United States Patent
Keller et al.

(10) Patent No.: US 7,772,415 B2
(45) Date of Patent: Aug. 10, 2010

(54) RADIATION ABSORBING COMPOSITIONS, METHODS AND ARTICLES INCORPORATING SUCH COMPOSITIONS

(75) Inventors: Keith A. Keller, Spartanburg, SC (US); Daniel M. Connor, Inman, SC (US); John G. Lever, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 11/451,028

(22) Filed: Jun. 12, 2006

(65) Prior Publication Data

US 2007/0117893 A1 May 24, 2007

Related U.S. Application Data

(63) Continuation-in-part of application No. 11/285,840, filed on Nov. 23, 2005.

(51) Int. Cl.
C07F 7/18 (2006.01)
C07F 7/02 (2006.01)
C08K 5/54 (2006.01)

(52) U.S. Cl. .......................... 556/9; 556/400; 524/188

(58) Field of Classification Search ................ 524/204, 524/398, 406, 409, 413, 188, 394; 556/400, 556/460, 9
See application file for complete search history.

(56) References Cited

U.S. PATENT DOCUMENTS

| | | | |
|---|---|---|---|
| 3,268,567 A | 8/1966 | Cyba | |
| 4,686,791 A | 8/1987 | Miyata | |
| 5,306,591 A * | 4/1994 | Larson et al. | 430/115 |
| 5,840,147 A | 11/1998 | Grimm | 156/272.2 |
| 5,843,265 A | 12/1998 | Grimm | 156/272 |
| 5,925,777 A | 7/1999 | Harada et al. | 556/1 |
| 6,153,779 A | 11/2000 | Hess et al. | 556/113 |
| 6,187,456 B1 | 2/2001 | Lever | 428/688 |
| 6,656,315 B2 | 12/2003 | Sallavanti et al. | 156/272.8 |
| 2007/0113967 A1 | 5/2007 | Connor et al. | |

FOREIGN PATENT DOCUMENTS

| | | |
|---|---|---|
| EP | 1 117 502 B1 | 1/2003 |
| WO | 2005/102672 | 4/2004 |
| WO | WO 2007/062183 A1 | 5/2007 |

OTHER PUBLICATIONS

Lyubchenko et al; 1996; Russian Journal of Chemistry; 22; 534-539.*
Bencini et al; 1998; Inorg. Chem., 37; 3719-3725.*
Hawley's Condensed Chemical Dictionary, 14th Edition, 2002.*
Ohkata et al; Synthesis of a New Dibenzocyclic Stiborane . . . ; Chemistry Letters; 1990; pp. 1721-1724.*
Inorg. Chem. Vo. 14, No. 11. 1975. Catechol Oxidations. Characterization of Metal Complexes of 3,5-Di-*tert*-butyl-1,2-quinone 1-(2-Hydroxy-3,5-di-*tert*-butylphenyl)imine Formed by the Aerial Oxidation of 3,5-Di-*tert*-butylcatechol in the Presence of Ammonia and Divalent Metal Ions.
Inorg. Chem. 1989, 28, 4379-4385. Charge Distribution in Transition-Metal Complexes of a Schiff Base Biquinone Ligand. Structural and Electrochemical Properties of the $M^{II}$ (Cat-N-BQ) (Cat-N-SQ), $M^{IV}$ (Cat-N-SQ)$_2$ Tautomeric Series.
Inorg. Chem. 1994, 33, 347-353. Iminoquinone Complexes of Iron and Nickel. Structural, Magnetic, and Electrochemical Properties of Complexes Containing the Phenoxazinolate Semiquinone Radical.
Inorg. Chem. 1996, 35, 3519-3524. Studies on Aerobic Reactions of Ammonia/3.5-DI-*tert*-butylcatechol Schiff-Base Condensation Products with Copper, Copper(I), and Copper(II). Strong Copper(II)—Radical Ferromagnetic Exchange and Observations on a Unique N-N Coupling Reaction.
Inorg. Chem. 1998, 37, 3719-3725. Density Functional Description of the Ferromagnetic Exchange Interactions between Semiquinonato Radicals Mediated by Diamagnetic Metal Ions.
Inorg. Chem. 1998, 37, 2296-2307. Electron Exchange and the Photophysics of Metal-Quinone Complexes. 1. Synthesis and Spectroscopy of Chromium-Quinone Dyads.
Inorg. Chem. 1999, 38, 2781-2790. Ligand-Based Redox Isomers of [$Zn^{II}$ ($C_{28}H_{20}NO_2$)$_2$]: Molecular and Electronic Structures of a Diamagnetic Green and a Paramagnetic Red Form.
Inorg. Chem. 2000, 39, 617-619. Redox-Tunable Valence Tautomerism in a Cobalt Schiff Base Complex.
Inorg. Chem 2003, 42, 6432-6440. Artic e. Temperature-Induced Solid-State Valence Tautomeric Interconversion in Two Cobalt-Schiff Base Diquinone Complexes.
J. Am. Chem. Soc. 1988. 110,1827-1832. Cobalt and Manganese Complexes of Schiff Base Biquinone Radical Ligand.
J. Am. Chem. Soc. 1994, 116, 1388-1394. Ferromagnetic Coupling between Semiquinone Type Tridentate Radical Ligands Mediated by Metal Ions.
Chem. Eur. J. 2004, 10, 5971-5976. Novel Hypervalent Complexes of Main-Group Metals by Intramolecular Ligand-Metal Electron Transfer.
Eur. J. Inorg. Chem. 1999, 1021-1027. Syntheses and Characterization by NMR Spectroscopy and X-ray Diffraction of Complexes Derived from Metals of Groups 2 and 13 and the Ligand Bis(3,5-di*tert*-butyl-1-hydroxy-2-phenyl)amine.

(Continued)

*Primary Examiner*—Vasu Jagannathan
*Assistant Examiner*—Karuna P Reddy
(74) *Attorney, Agent, or Firm*—Robert M. Lanning

(57) ABSTRACT

Infrared (IR) radiation absorbing compounds of metal or metalloids with ligands are beneficial for many applications. Schiff base biquinone (SBB) ligands surrounding a metal or metalloid center may be used for laser welding applications, as one example, wherein effective infared radiation absorption and heat resistance are required. These compounds may be known as Schiff base biquinone metal complexes (SB-BC's). The compositions and methods of this invention provide examples of many different NIR absorbing compounds that exhibit high NIR absorbing strength, good thermal stability, and relatively low visible color. The IR absorbing compounds may employ one or more of the following elements: Si, Zr, Bi, Sb, Ce, Cs, K, Mo.

5 Claims, No Drawings

OTHER PUBLICATIONS

DT/SO. Phosphorus. Sulfur. And Silicon. 1994. vol. 91 pp. 189-203. Syntheses, Characterization and Reactivity of Dibenzobicyclic Phosphoranes 10-P-5.

Stegmann und Scheffler. Chem Ber. 101, 262-271 (1968). Hartmut B. Stegmann und Klaus Scheffler. ESR-Untersuchungen einer Modell-Phenoxazinsynthese.

Milliken Pending Application. U.S. Appl. No. 11/285,840, (Milliken file 5906) applicant—Connor et al., filed on Nov. 23, 2005. Title: "Radiation absorbing compositions, methods and articles made by applying such compositions".

Cador, O. et al. *Inorg. Chem.* 2003, 42, 6432-40.

Girgis, A.Y. et al. *Inorg. Chem.* 1975, 14, 2724-27.

Maiya, B.G. et al. *J. Chem. Soc. Dalton Trans.*, 1990, 3571-76.

Speier, G. et al. *Inorg. Chem.* 1996, 35, 3519-24.

Tanski, J.M. et al. *Dalton Trans.*, 2005, 2442-2447.

* cited by examiner

RADIATION ABSORBING COMPOSITIONS, METHODS AND ARTICLES INCORPORATING SUCH COMPOSITIONS

CROSS REFERENCE TO RELATED APPLICATION

This application is a continuation-in-part (CIP) of prior U.S. application Ser. No. 11/285,840 (Milliken & Company File No. 5906) entitled "RADIATION ABSORBING COMPOSITIONS, METHODS, AND ARTICLES MADE BY APPLYING SUCH COMPOSITIONS", filed in the United States Patent and Trademark Office on Nov. 23, 2005.

BACKGROUND OF THE INVENTION

Infrared (IR) radiation absorbing compounds are beneficial for many applications. They are useful in optical recording media, thermal writing display, laser printing, laser filters, IR photography, medical applications, plastic reheat, laser welding, laser marking and for protective goggles for welding and for protection from lasers in military applications. Several classes of IR absorbing compounds are known including carbon black, inorganic pigments, metals, organic dyes, and organic pigments.

Many classes of organic IR dyes are known including squaric acid dyes, croconic acid dyes, imminium dyes, cyanines, anthraquinones, quaterylenes, perylenes, porphryins, triphenylmethanes, polymethines, quinine dyes, azos, and others. Organometallic IR absorbers are also known including metal phthalocyanine, metal naphthocyanine, and metal dithiolenes. A thorough review of IR absorbing compounds has been published (*Chem. Rev.* 1992, 92, 1197-1226).

Infrared radiation is commonly defined as "light" with wavelength greater than 700 nm and less than 1 mm. Near IR (NIR) light is commonly defined as radiation with a wavelength between 700 nm and 14,000 nm. The majority of common NIR absorbing dyes and pigments have maximum IR absorbance between 700 nm and 3000 nm. Most common NIR dyes absorb between about 700 nm and 1500 nm. Compounds such as carbon black, which are black-body absorbers, absorb over a very broad wavelength range.

It is highly desirable for NIR absorbing compounds to have strong NIR absorbance yet have minimal visible light absorbance (i.e., absorbance between 400 nm and 700 nm). These compounds are advantageous for use in non-colored and lightly colored transparent applications where strong NIR absorption without strong color is desired. Some advantageous NIR compounds are mostly transparent to visible light in liquid or plastic compositions.

To be highly useful in many applications, a NIR absorber must have several properties in addition to absorption at the desired wavelength. The absorption efficiency must be sufficiently strong (as characterized by the molar absorptivity constant). The compound(s) should be sufficiently soluble or compatible in the medium in which it is used. Further, the compound should be sufficiently thermally and oxidatively stable to facilitate incorporation and use in the desired application without excessive degradation during the desired lifetime of the absorber.

Transmission laser welding is a well known method for joining thermoplastic articles. In one embodiment of this technique an IR laser beam is passed through an IR transparent part and impinges on a second part containing IR absorbing species. These IR absorbing species can be contained in the bulk of the polymer through melt mixing or applied to the interface between the two parts as a coating. The IR absorbing species absorbs sufficient energy from the laser to melt the surrounding plastic. The molten plastic from the two parts flows together and cools to form a strong joint or weld. It is necessary for the IR absorbing species to be thermally stable enough to survive for a brief period of time in the molten polymer. A higher level of thermal stability is needed for incorporation of the IR absorbing compound into the molten polymer during the fabrication of the article. It is particularly advantageous for the IR absorbing compound to impart minimal color. in or on the resulting part, although this is not always necessary. Thus, there is a need in this industry for compounds that will afford the correct absorption characteristics, and also exhibit a high level of thermal stability, while imparting minimal color upon welded parts or seams. Few NIR dyes have the correct combination of properties for incorporation into thermoplastic media or to be used for laser welding via a coating. Of the few that are known, cyanine, imminium/diimonium, quaterylenes, metal dithiolenes, and squaryliums are most common. Many of these compounds are difficult and expensive to make.

There exists therefore a strong need for new and improved IR absorbing compounds. There is a need in the industry for NIR absorbing compounds that are easy to manufacture, with sufficient thermal stability for incorporation into plastic. Such compounds may be used for many different applications, including for example for laser welding through a coating. It would be desirable to incorporate compounds that provide a relatively low visible absorption and impart minimal color to articles in which they are incorporated.

DETAILED DESCRIPTION OF THE INVENTION

In the practice of the invention, it is possible to employ compounds as IR absorbers and as additives for plastics in a manner which has not been recognized to date. Below is a compound of general Formula 1, in which $R_1$-$R_4$ may be the same or different and consist of alkyl, branched alkyl, cycloalkyl, aryl, substituted aryl, heteroaryl, alkoxy, halogen, dialkylamino, polyoxyalkylene, carboxyl, acyl, or hydrogen. Some $R_1$-$R_4$ groups that may be particularly useful include: methyl, ethyl, isopropyl, tert-amyl, isobutyl, and tert-butyl.

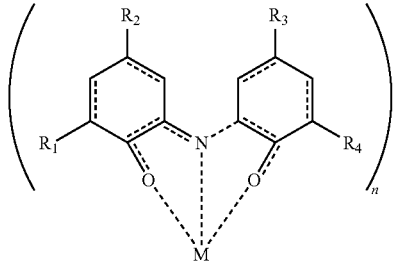

Formula 1

These compounds are characterized by Schiff base biquinones (SBB) surrounding a metal center. The structure in Formula 1 is intended to encompass any of numerous oxidation states, electronic states, resonance forms, or tautomers. In the chemical literature these SBB ligands are known as stable dianionic semiquinonato radicals, monoanionic dienones with no unpaired electrons, or other canonical forms. These compounds can be termed Schiff base biquinone metal complexes (SBBCs). A number of metal centers have been disclosed for SBBC complexes and these complexes are known to exist in a number of oxidation states. However, such compositions comprising SBBCs in thermoplastics or thermoset polymers are not known, nor have they been disclosed for use in laser welding, laser filters, laser marking, as compositions in such IR absorbing coatings, or for the dyeing of textile materials, as examples. Compounds described by Formula 1 or Formula 2 in which M=Si, Zr, Bi, Sb, Ce, Cs, K, or Mo are disclosed herein.

In some instances, a di-alkyl substituted catechol is a useful group to employ in the synthesis of compounds of the invention. Also, since $R_1$-$R_4$ may be hydrogen, there is a good selection of monosubstituted catechols that may be employed in the practice of the invention. In the Formula 1 above, n is from about 1 to about 4.

Catechols based on 3,5-di-alkyl substituted catechol (1,2-dihydroxybenzene) may be employed, including for example: 3-methyl-5-isopropyl, 3,5-dimethyl, 3-methyl-5-ethyl, 3-methyl-5-t-butyl, 3-t-butyl-5-methyl, 3,5-disopropyl, 5-methyl-3-(1,1,3,3-tetramethylbutyl), 3-t-butyl-5-t-octyl, 5-t-butyl-3-(1,1-dimethylhexyl), 3,5-didodecyl, 3-methyl-5-propyl, 3,5-bis-(2,2-dimethyl-propyl), 5-(1,1-dimethyl-hexyl)-3-methyl, 3-methyl-5-(1,1,3,3-tetramethyl-butyl), 3,5-di-t-amyl, 3-(1,1-dimethyl-hexyl)-5-methyl, 3-t-butyl-5-t-octyl, 5-t-butyl-3-t-octyl, 3,5-bis-(1,1-dimethyl-hexyl), 3,5-Bis-(1,1,3,3-tetramethyl-butyl), 3-Methyl-5-(1,1,3,3,5,5-hexamethyl-hexyl), 5-methyl-3-(1,1,3,3,5,5-hexamethyl-hexyl), 5-methyl-3-pentadecyl, 3,5-di-n-propyl, 3-isopropyl-5-(1,1,3,3-tetramethyl-butyl), 5-t-butyl-3-methyl, 5-methyl-3-t-butyl, 3-t-butyl-5-isopropyl, 3-isopropyl-5-t-butyl, 3,5-dioctadecyl, 3-t-butyl-5-ethyl, 3-t-butyl-5-isopropyl, 3,5-di-n-dibutyl, 3,5-di(1,1,2,2-tetramethylpropyl), and 3,5-di-2-ethylhexyl.

Monoalkyl substituted catechol compounds can be employed as well, including for example: 3-methyl, 5-methyl, 3-ethyl, 5-ethyl, 3-isopropyl, 5-isopropyl, 3-n-propyl, 5-n-propyl, 3-butyl, 5-butyl, 3-sec-butyl, 5-sec-butyl, 3-t-butyl, 5-t-butyl, 3-(1-methylbutyl), 5-(1-methylbutyl), 3-amyl, 5-amyl, 3-(1,1,3,3-tetramethylbutyl), 5-(1,1,3,3-tetramethylbutyl), 3-(2,2-dimethylpropyl), 5-(2,2-dimethylpropyl), 3-(2-ethylhexyl), 5-(2-ethylhexyl), 3-(1,1-dimethylhexyl), 5-(1,1-dimethylhexyl), 3-t-amyl, 5-t-amyl, 3-(1,1,3,3,5,5-hexamethyl-hexyl), 3-(1,1,2,2-tetramethylpropyl), 5-(1,1,2,2-tetramethylpropyl), 3-hexyl, 5-hexyl, 3-heptyl, 5-heptyl, 3-octyl, and 5-octyl This invention provides examples of many different NIR absorbing compounds that exhibit high NIR absorbing strength, good thermal stability, and low visible color. These NIR absorbers may have application in optical recording media, thermal writing, dying of textile materials, electronic display, laser printing, laser filters, IR photography, medical applications, plastic reheat, laser welding, laser marking and for protective goggles for welding and for protection from lasers in military applications.

The invention may provide a wide range of compositions of matter. A compound described by Formula 1 in which M=Si, Zr, Bi, Sb, Ce, Cs, K, or Mo element in any oxidation state, valence, or electronic state. $R_1$-$R_4$ may be the same or different and may be comprised of: alkyl, branched alkyl, cycloalkyl, aryl, substituted aryl, heteroaryl, alkoxy, halogen, dialkylamino, polyoxyalkylene, carboxyl, acyl, or hydrogen. Species that may be quite useful for $R_1$-$R_4$ include, among others: methyl, ethyl, isopropyl, isobutyl, tert-amyl, and tert-butyl. When an alkyl is employed, the alkyl may be methyl, ethyl, isopropyl, butyl, isobutyl, tert-amyl, and tert-butyl, as examples.

A thermoplastic or thermoset composition containing the compound of Formula 1 above may be employed. The metal-like species ("M" in Formula 1 or 2) may be Si, Zr, Bi, Sb, Ce, Cs, K, or Mo in any oxidation state, valence, or electronic state. $R_1$-$R_4$ may be the same or different (independent) and are comprised of: alkyl, branched alkyl, cycloalkyl, aryl, substituted aryl, heteroaryl, alkoxy, halogen, dialkylamino, polyoxyalkylene, carboxyl, acyl, or hydrogen. Species that may be quite useful for $R_1$-$R_4$ include, among others: methyl, ethyl, isopropyl, isobutyl, tert-amyl, and tert-butyl.

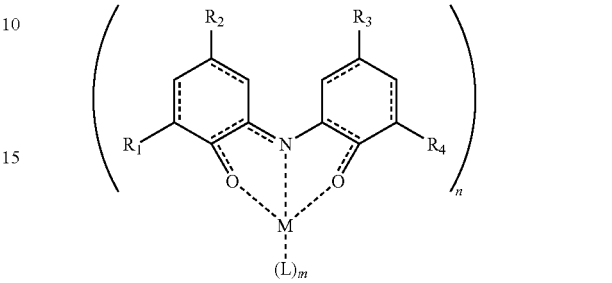

Formula 2

A composition shown in Formula 2 is also disclosed for such use, in which M=Si, Zr, Bi, Sb, Ce, Cs, K, or Mo element in any oxidation state, valence, or electronic state. $R_1$-$R_4$ may be the same or different and consist of one or more of: alkyl, branched alkyl, cycloalkyl, aryl, substituted aryl, heteroaryl, alkoxy, halogen, dialkylamino, polyoxyalkylene, carboxyl, acyl, or hydrogen. Species that may be quite useful include: methyl, ethyl, isopropyl, isobutyl, tert-amyl, and tert-butyl. In the Formula 2 above, n is from about 1 to about 4, and m is also from about 1 to about 4.

A thermoplastic or thermoset comprising the compound shown in Formula 2 is disclosed as well, in M=Si, Zr, Bi, Sb, Ce, Cs, K, or Mo element in any oxidation state, valence, or electronic state and in which $R_1$-$R_4$ may be the same or different and consists of alkyl, branched alkyl, cycloalkyl, aryl, substituted aryl, heteroaryl, alkoxy, halogen, dialkylamino, polyoxyalkylene, carboxyl, acyl, or hydrogen. Species that may be quite useful include: methyl, ethyl, isopropyl, isobutyl, tert-amyl, and tert-butyl. In the Formula 2 above, n is from about 1 to about 4, and m is also from about 1 to about 4.

In the compound of Formula 2, additional ligands $(L)_m$ may also be present around the metal or metalloid center in compounds as in Formula 2, such as (but not limited to) the following: alkyl, alkene, allyl, alkynyl, pyridine, bipyridine, terpyridine, chloride or other halogens, perchlorate, sulfate, phosphate, organophosphate, phosphines, cyclopentadienyl, acetate, malonate, alkanoate, benzoates, acetylacetonate, alkoxide, oxide, Schiff bases, amines, imines, thiols, diamines, thiolenes, indoanilines, azos, formazyls, phthalocyanines, phenyl, substituted phenyl, and merocyanines, carbonyl, cyano, oxo, carboxyl, aqua, hydroxo, sulfato, sulfito, nitrito, nitro, nitrosyl, isothiocyanato, thiosulfato, ethylene diamine, oxalato, ethylene diamine tetraacetic acid, cabonato, amido, imido, nitrido, ammino, peroxo, phosphato, phosphito, phosphido, borato, sulfido, porphyrin, monoximes, crown ethers, cryptates, chromato, chromito, hydrido, cyclypentyldieno, aryls, polyoxyalkylene and thiacyls. L may represent one or more ligands and may be the same or different. In some preferred embodiments, L may represent at least one alkyl group, at least one aromatic group, at least one substituted aromatic group, at least one alkoxy group, at least one polyoxyalkylene group, or at least one halogen. L may also represent one repeat unit or side chain of a larger polymeric structure. The "m" may be from about 1 to about 4.

Compositions useful for applications described herein may include as well coloring agents, ultraviolet absorbers, light stabilizers, acid scavengers, bluing agents, color-correction agents, anti-microbial agents, slip agents, plasticizers, impact modifiers, anti-oxidants, fillers, clarifiers, nucleating agents, or mixtures thereof, as liquids or as pellets for further introduction within desired molten thermoplastic or thermoset formulations (or precursor formulations). Methods of making such compositions, particularly thermoplastics, comprising such compounds of are also contemplated within this invention.

The "M" in Formulas 1 or 2 may be Si, Zr, Bi, Sb, Ce, Cs, K, or Mo in any oxidation state, valence, or electronic state. Examples are shown herein at Table 1. These metals, metalloids, or semiconductors may have particular application when applied with catechols based on 3,5-di-alkyl substituted catechol (1,2-dihydroxybenzene).

Formula 3

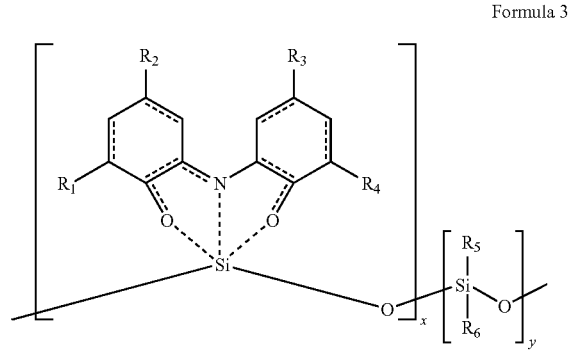

Another novel composition is a polysiloxane compound comprising the polymer segment disclosed in Formula 3, where $R_1$-$R_4$ may be the same or different and may be comprised of: alkyl, branched alkyl, cycloalkyl, aryl, substituted aryl, heteroaryl, alkoxy, halogen, dialkylamino, polyoxyalkylene, carboxyl, acyl, or hydrogen. Species that may be quite useful for $R_1$-$R_4$ include, among others: methyl, ethyl, isopropyl, isobutyl, tert-amyl, and tert-butyl. When an alkyl is employed, the alkyl may be methyl, ethyl, isopropyl, butyl, isobutyl, tert-amyl, and tert-butyl, as examples. In Formula 3, $R_5$ and $R_6$ may be the same or different and consist of one or more of: alkyl, branched alkyl, cycloalkyl, aryl, alkynyl, substituted aryl, heteroaryl, alkoxy, halogen, dialkylamino, polyoxyalkylene, polysiloxane, carboxyl, acyl, or hydrogen. X and y represent the mole fraction of each repeat unit. X may range from about 0.000001 to about 1 and y may range from about 0 to about 0.999999. These polymeric NIR dyes provide the opportunity for tuning various physical and chemical properties such as solubility, melting point, and the like.

The term "thermoplastic" is intended to encompass any synthetic polymeric material that exhibits a modification in physical state from solid to liquid upon exposure to sufficiently high temperatures. Most notable of the thermoplastic types of materials are polyolefins (i.e., polypropylene, polyethylene, and the like), polyester (i.e., polyethylene terephthalate, polybutylene terephthalate, polytrimethylene terephthalate, and the like), polyamides (i.e., nylon-1,1, nylon-1,2, nylon-6 or nylon-6,6), polystyrenes, polycarbonates, polyvinyl halides (i.e., polyvinyl chloride and polyvinyl difluoride), polylactic acid, acrylate polymers, as examples). Thermoplastics that are readily employed in the practice of the invention include polypropylene, polystyrene, polymethylmethacrylate, polycarbonate, nylon, polyethylene, and polyester.

Thermoplastic articles that may benefit from application of the compounds of the invention may include (without limit) bottles, storage containers, sheets, films, fibers, plaques, hoses, tubes, syringes, medical devices, and electronics components. Included are polyester, polystyrene, polycarbonate, polyacrylates, and other like resinous materials in sheet form which are present within windows for strength and resiliency functions. In such an instance, the inventive NIR absorbing compounds provide or contribute to excellent IR absorption to such thermoplastic articles for decorative, aesthetic or protective purposes. The possible uses for such NIR absorbers for such items as thermoplastics are many. Possible end-uses include use of such compounds within solvent systems, printing inks, within and with textiles (either on or within textiles, fibers, or fabrics) within display devices such as liquid crystal displays, in or on electronic recording media.

The inventive NIR absorbing compounds may be added in any amount to such thermoplastics as is needed to provide beneficial results. The amount may be between about 0.00001 ppm to about 25,000 ppm per total amount of resin; in some instances from about 0.001 and about 15,000 ppm; in other applications may be between about 0.1 to about 5,000 ppm; and in still other applications from about 100 to about 2,500 ppm. The more NIR absorber present, the stronger IR absorption therein.

The term "thermoset" or "thermosets" refers to a polymeric solid which upon exposure to sufficient heat or in the presence of a sufficient amount of catalyst, configures itself into a pre-determined shape. Foams, sheets, articles, coverings, and the like are all possible, and are within the scope of the invention. Examples of such thermosets include polyurethane, epoxies, phenolic resins, unsaturated polyester systems, thermoset polycarbonates and the like.

The inventive NIR absorbing compounds may be added in any amount to such thermosets up to their saturation limits. The amount may be between about 0.00001 ppm to about 25,000 ppm per total amount of resin; in other aspects, may be from about 0.001 to about 15,000 ppm; in other applications may be between about 0.1 to about 5,000 ppm. The more NIR absorber present in a composition, the stronger the IR absorption therein. When mixed with other colorants within the target thermoset, the same amounts may be used within the saturation limit, i.e. dependent upon the amount of any extra colorants therein.

Thermoplastic or thermoset IR absorbers (and other additives) are added to such compositions during the injection molding (or other type of molding, such as blow molding) and without limitation, by mixing the absorber with resin pellets and melting the entire coated pellets, or through a masterbatch melting step while the resin and absorber are pre-mixed and incorporated together in pellet form. Such plastics include for example polyolefins, polyesters, polyamides, polyurethanes, polycarbonates, and other well known resins. Generally, such plastics, including the IR absorber, colorant, UV absorber, and other potential additives, are formed by way of any number of extrusion techniques.

In one application of the invention, at least a first and second polymeric article is provided. The compounds as described herein in Formula 1 and/or 2 may be applied upon, or more likely within, the polymeric article. The polymeric article may be a thermoplastic, or polyolefin, or other compound. The articles are placed closely together. Then, radiation such as laser radiation is applied. The compound absorbs the radiation, and forms heat which melts a portion of the polymeric articles. Then, the radiation is removed, thereby bonding the first polymeric article to the second polymeric article.

In yet another embodiment of the invention, a textile or a fabric may receive a deposit of such compounds as in Formula 1 or 2. A fabric or textile of reduced IR reflectance can be made. Such a fabric may be useful as electronic for avoiding infared detection of items positioned within or behind the fabric.

Another embodiment of this invention includes compositions comprising the inventive IR absorbers of Formula 1 or 2 in solutions or dispersions suitable for application to solid substrates such as thermoplastics, thermosets, paper, or textile articles, including fabrics. Such compositions may include solvents, dispersing agents, coagulants, thickening agents, colorants, chelating agents, and the like. Such solutions or dispersions may be solvent or aqueous based and may be useful for applying the inventive IR absorbers to plastic parts for laser welding and to fabrics for improved IR absorption. Such solutions designed for use in applications such as optical recording media, thermal writing displays, laser printing, laser filters, IR photography, medical applications, plastic reheat, laser welding, laser marking and for protective goggles for welding and for protection from lasers in military applications are also envisioned within the scope of the invention.

In one embodiment, a hydrotalcite compound such as DHT-4A® from Mitsui and Company may be employed, as further set forth in examples below. This compound may assist in the radiation welding applications, as well as in other applications. This compound may enhance the thermal stability of the inventive IR absorbers in some applications.

The novel described metal centered IR absorbers offer significant advantages in color and cost. Absorbers are suitable for polymer reheat with low color, laser imaging, laser light protection, laser welding plastics with low color, and for many other applications. The compounds used in the prior art are expensive and often have high color and low thermal stability.

Reference now will be made to the embodiments of the invention, one or more examples of which are set forth below. Each example is provided by way of explanation of the invention, not as a limitation of the invention. In fact, it will be apparent to those skilled in the art that various modifications and variations can be made in this invention without departing from the scope or spirit of the invention.

EXAMPLES

General Procedure for the Preparation of SBBC Compounds (Direct Formation)

3,5-di-tert butyl-catechol (4.5 equivalents) was combined with a metal salt (1 equivalent), and 28% aqueous ammonium hydroxide (about 30 equivalents) in an ethanol solvent. The mixture was stirred overnight at room temperature with an air sparge. The material was filtered, washed with water, washed with ethanol, and dried. Recrystallization from chloroform/ethanol was sometimes needed. In some cases it was necessary to hot-filter the recrystallization solutions to remove insoluble materials.

General Procedure for the Preparation of SBBC Compounds (Transmetallation)

The transmetallation route is exemplified by using the Zn SBBC to synthesize the Sb SBBC. Zn SBBC (1.0 g), SbCl$_3$ (0.25 g), and methylene chloride (30 mL) were stirred at room temperature overnight with an air sparge. Water (25 mL) was added and the organic layer was collected using a separatory funnel. Ethanol was added to precipitate the product. Yield was 0.25 g.

Procedure for the Preparation Of Si(SBBC)

3,5-di-t-butylcatechol (133.96 g) was dissolved in 833 mL of dry isopropyl alcohol. Tetraethylorthosilicate (17.36 g) was added followed by ammonia (7N) in methanol (394 mL). Dry air was purged through the liquid for 2 days followed by filtration to yield the Si SBBC (47.15 g), A small portion of the product was purified by Soxhlet extraction into methylene chloride and recrystallized from methylene chloride. λmax 982 (THF), mp=>350° C.

Procedure for the Preparation of Si(SBBC)Me$_2$ 3,5-di-t-butylcatechol (33.49 g) was dissolved in 208 mL of dry isopropyl alcohol. Dichlorodimethylsilane (2.70) was added followed by ammonia (7N) in methanol (98.4 mL). Dry air was purged through the liquid for 2 days followed by filtration to yield the Si SBBC-Me$_2$ IR dye (3.14 g). $\lambda_{max}$ 982.

Procedure for the Preparation of Si(SBBC)Ph$_2$ 3,5-di-t-butylcatechol (33.49 g) was dissolved in 208 mL of dry isopropyl alcohol. Dichlorodiphenylsilane (5.27 g) was added followed by ammonia (7N) in methanol (98.4 mL). Dry air was purged through the liquid for 2 days followed by filtration to yield the Si SBBC-Phe$_2$ IR dye (3.50 g). $\lambda_{max}$ 982

Procedure for the Preparation of Poly(SBBC Siloxane)

3,5-di-t-butylcatechol (33.49 g) was dissolved in 208 mL of dry isopropyl alcohol. Poly(diethoxysiloxane) (5.63 g) was added followed by ammonia (7N) in methanol (98.4 mL). Dry air was purged through the liquid for 2 days followed by filtration to yield the poly(SBBC siloxane)IR dye (15.41 g). $\lambda_{max}$ 982

TABLE 1

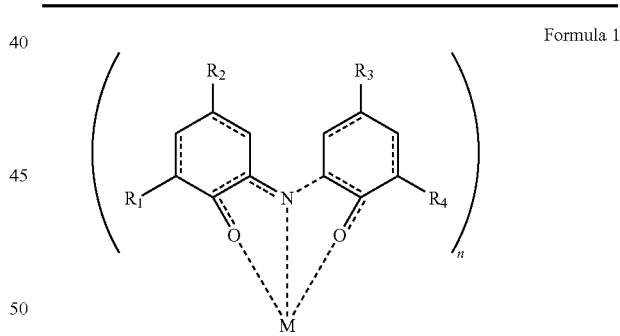

Formula 1

Various Metals and Lambda Max Values for IR Absorbers of Formula 1

| Example # | Metal Used | Metal Source (M) | Lambda Max in IR (nm) |
|---|---|---|---|
| 1 | Antimony | SbCl$_3$ | 1066 |
| 2 | Bismuth | Bi(NO$_3$)•5H$_2$O | 780 |
| 3 | Cerium | Ce(NO$_3$)$_3$•6H$_2$O | 855, 865 |
| 4 | Cesium | CsCl | 801 |
| 5 | Molybdenum | MoCl$_5$ | 847 |
| 6 | Potassium | KCl | 801 |
| 7 | Silicon | Si(OEt)$_4$ | 982 |
| 8 | Zirconium | ZrOCl$_2$•8H$_2$O | 836 |

TABLE 2

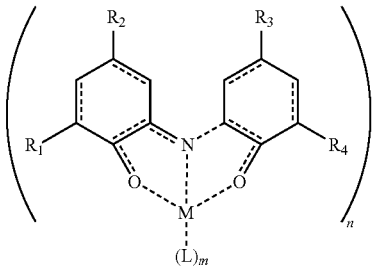

Various Metals and Lambda Max Values for IR Absorbers of Formula 2

| Example # | Metal Used | Metal Source (M) | L | Lambda Max in IR (nm) |
|---|---|---|---|---|
| 9 | Si | Si(CH$_3$)$_2$(Cl)$_2$ | CH$_3$, CH$_3$ | 982 |
| 10 | Si | Si(Ph)$_2$(Cl)$_2$ | Ph, Ph | 982 |

Plastic Compositions

For many of the compounds in this class, the absorption in the NIR can be broad so the reported absorption maxima in the examples are only reported as approximate values. Lambda Max values reported herein are typical of those measured on UV-Vis Spectrophotometric apparatus.

Polypropylene (PP)

The following formulation was used to compound the inventive IR absorbers into polypropylene for extrusion.

| | |
|---|---|
| Polypropylene homopolymer - (12 MFI) | 995.2 g |
| Millad 3988 ® (Milliken Chemical) | 2.5 g |
| Irganox 1010 ® (Ciba Specialty Chemical) | 1.0 g |
| Irgafos 168 ® (Ciba Specialty Chemical) | 1.0 g |
| DHT-4A (Mitsui & Co.) | 0.2 g |
| Inventive IR absorber | 0.1-1.0 g |

The additives and the polymer pellets were mixed thoroughly. The material was compounded on a 16 mm Prism co-rotating twin screw extruder with a length/diameter ratio of 25:1. The temperature set-points for the heaters for running all PP examples was 210-220° C.

Injection Molding Polypropylene (PP) Plaques

The PP resin which had been compounded with the inventive IR absorbing additives was injection molded on an Arburg 221-75-350 40-ton injection molding machine with a barrel temperature of 230° C. The pellets were gravity fed into the feed throat of the machine. In the feed section, melting was accomplished through the utilization of a heated (heat transferred from the barrel of the machine) screw extruder which rotated. The rotation of the screw provided thorough mixing of the additive and molten resin together producing a uniform plastic melt which was injected into a mold in order to form the thermoplastic article, for instance a 2 inch by 3 inch plaque with a uniform thickness of 50 mils. Plaques were used for gathering spectroscopic data in the table.

TABLE 3

SBBC-Polypropylene Compositions (Injection Molded Plaques)

| Example # | Dye Example # from Table 1 | Metal | Loading (ppm) | Lambda Max in IR |
|---|---|---|---|---|
| 10 | 8 | Zr | 1000 | 722 |
| 11 | 7 | Si | 520 | 980 |
| 12 | 3 | Ce | 1000 | 790 |

Extrusion of Polyethylene Terephthalate (PET)

PET pellets (M&G 8006) were dried to a water level of less than 50 ppm and mixed with the inventive IR absorbers on a Hobart mixer. The additives and the polymer pellets were mixed thoroughly. The material was compounded on a 16 mm Prism co-rotating twin screw extruder with a length/diameter ratio of 25:1. The temperature set-points for the heaters for running all PP examples was 250-270° C. 200 ppm of inventive IR absorber and 2500 ppm DHT4A were used in all formulations.

Example 13

The PET Compound Containing the Dye from Example 8 Showed the Characteristic Slight Green Shade Example 14

The PET Compound Containing the Dye from Example 7 Showed the Characteristic Slight Pink Shade.

PET Film

The pellets produced in examples 13 and 14 were extruded into a 1.5 mil thick film.

TABLE 4

SBBC-PET Compositions (Film)

| Example # | Polymer from Example # | Metal | Loading (ppm) | Lambda Max in IR |
|---|---|---|---|---|
| 15 | 13 | Zr | 200 | Decomposed |
| 16 | 14 | Si | 200 | 980 |

Injection Molding PET-G Plaques

PET-G pellets (Eastman Eastar® 6723) were dried to a water level of less than 50 ppm and mixed with the inventive IR absorbers on a Hobart mixer. The additives and the polymer pellets were mixed thoroughly. The pellets produced in examples 13 and 14 were injection molded on an Arburg 220M-35-90 40-ton injection molding machine with a barrel temperature of 540-550° F. The pellets were gravity fed into the feed throat of the machine. In the feed section, melting was accomplished by utilization of a heated (heat transferred from the barrel of the machine) screw extruder which rotated. The rotation of the screw provided thorough mixing of the colorant and molten resin together producing a uniform plastic melt which was injected into a mold in order to form the thermoplastic article, for instance a 2 inch by 3 inch plaque with a uniform thickness of 50 mils. 5000 ppm DHT4A was used in all formulations.

TABLE 5

SBBC-PET-G Compositions (Injection Molded Plaques)

| Example # | Dye Example # from Table 1 | Metal | Loading (ppm) | Lambda Max in IR |
|---|---|---|---|---|
| 17 | 8 | Zr | 285 | 830 |
| 18 | 7 | Si | 230 | 987 |
| 19 | 2 | Bi | 250 | Decomposed |

SBBC compounds of formula 1 or formula 2 in which M=Si or Zr have shown unexpectedly and advantageously high thermal stability in some thermoplastic resins.

Injection Molding Polystyrene Plaques

Polystyrene pellets (Atofina PS500) were mixed with the inventive IR absorbers on a Hobart mixer. The additives and the polymer pellets were mixed thoroughly. The pellets were injection molded on an Arburg 220M-35-90 40-ton injection molding machine with a barrel temperature of 215° C. The pellets were gravity fed into the feed throat of the machine. In the feed section, melting was accomplished by utilization of a heated (heat transferred from the barrel of the machine) screw extruder which rotated. The rotation of the screw provided thorough mixing of the dye and molten resin together producing a uniform plastic melt which was injected into a mold in order to form the thermoplastic article, for instance a 2 inch by 3 inch plaque with a uniform thickness of 50 mils.

TABLE 6

SBBC-PS Compositions (Injection Molded Plaques)

| Example # | Dye Example # from Table 1 | Metal | Loading (ppm) | Lambda Max in IR |
|---|---|---|---|---|
| 20 | 8 | Zr | 240 | 722 |
| 21 | 7 | Si | 360 | 980 |
| 22 | 2 | Bi | 405 | Decomposed |

Injection Molding PC Plaques

Polycarbonate (Bayer Makrolon® 2407), DHT-4A (2000 ppm) was dried and mixed with the inventive IR absorbers (500 ppm) and DHT-4A (2000 ppm) on a Hobart mixer. The mixtures were injection molded on an Arburg Allrounder® injection molding machine with a barrel temperature of 277° C. The pellets were gravity fed into the feed throat of the machine. In the feed section, melting was accomplished by utilization of a heated (heat transferred from the barrel of the machine) screw extruder which rotated. The rotation of the screw provided thorough mixing of the colorant and molten resin together producing a uniform plastic melt which was injected into a mold in order to form the thermoplastic article, for instance a 2 inch by 3 inch plaque with a uniform thickness of 50 mils.

TABLE 7

SBBC-PC Compositions (Injection Molded Plaques)

| Example # | Dye Example # from Table 1 | Metal | Loading (ppm) | Lambda Max in IR |
|---|---|---|---|---|
| 23 | 7 | Si | 200 | 981 |

Injection Molding Thermoplastic Elastomer (TPE) Plaques

Thermoplastic elastomer (Dynaflex® G2712) was dried and mixed with the inventive IR absorbers (500 ppm) on a Hobart mixer. The mixtures were injection molded on an Arburg 220M-35-90 40-ton injection molding machine with a barrel temperature of 400° F. The pellets were gravity fed into the feed throat of the machine. In the feed section, melting was accomplished by utilization of a heated (heat transferred from the barrel of the machine) screw extruder which rotated. The rotation of the screw provided thorough mixing of the colorant and molten resin together producing a uniform plastic melt which was injected into a mold in order to form the thermoplastic article, for instance a 2 inch by 3 inch plaque with a uniform thickness of 50 mils.

TABLE 8

SBBC-TPE Compositions (Injection Molded Plaques)

| Example # | Dye Example # from Table 1 | Metal | Loading (ppm) | Lambda Max in IR |
|---|---|---|---|---|
| 24 | 7 | Si | 500 | 987 |
| 25 | 8 | Zr | 500 | 722 |

Extrusion of Transparent ABS

Transparent ABS (Chi Mei Polylac® PA 758) was dried and mixed with the inventive IR absorbers (500 ppm) on a Hobart mixer. The material was compounded on a 16 mm Prism co-rotating twin screw extruder with a length/diameter ratio of 25:1. The temperature set-points for the heaters for running all ABS examples was 200-230° C. 200 ppm of inventive IR absorber and 2500 ppm DHT4A were used in all formulations.

Example 26

The ABS Compound Containing the Dye from Example 8 (Zr) Showed the Characteristic Slight Green Shade.

Example 27

The PET Compound Containing the Dye from Example 7 (Si) Showed the Characteristic Slight Pink.

TABLE 9

SBBC-Transpartent ABS Compositions (Injection Molded Plaques)

| Example # | Dye Example # from Table 1 | Metal | Loading (ppm) | Lambda Max in IR |
|---|---|---|---|---|
| 26 | 8 | Si | 200 | 1005 |
| 27 | 7 | Zr | 200 | 818 |

Extrusion of Polyethylene (PE)

Polyethylene copolymer (Dow "Engage 8401") was mixed with the inventive infa-red (IR) absorbers (500 ppm) on a Hobart mixer. The material was compounded on a 16 mm Prism co-rotating twin screw extruder with a length/diameter ratio of 25:1. The temperature set-points for the heaters for running all PE examples was 170-190° C. 200 ppm of inventive IR absorber and 2500 ppm DHT4A were used in the formulations.

TABLE 10

SBBC-PE Compositions (Injection Molded Plaques)

| Example # | Dye Example # from Table 1 | Metal | Loading (ppm) | Lambda Max in IR |
|---|---|---|---|---|
| 28 | 7 | Si | 200 | 985 |

Laser Welding

TPE plaques from examples above can be transmission laser welded to control TPE plaques (50 mil), and bonded. A method of joining two polymeric articles is contemplated in which a first polymeric article and a second polymeric article may be fused or melted together in a weld. At least one of the polymeric articles contains a compound as set forth above in Formula 1 or 2, in which IR radiation absorbing compounds assist in the absorption of IR radiation which cause melting which cause the formation of a bond or weld. The articles are placed together, and then radiation is applied to the polymeric articles. The compound within or upon one of the articles absorbs the radiation, which heats and melts a portion of said first or said second polymeric articles. Then, when the radiation is removed there is bonding of the first polymeric article to the second polymeric article.

It is understood by one of ordinary skill in the art that the present discussion is a description of exemplary embodiments only, and is not intended as limiting the broader aspects of the present invention, which broader aspects are embodied in the exemplary constructions. The invention is shown by example in the appended claims.

The invention claimed is:

1. A compound, said compound comprising:

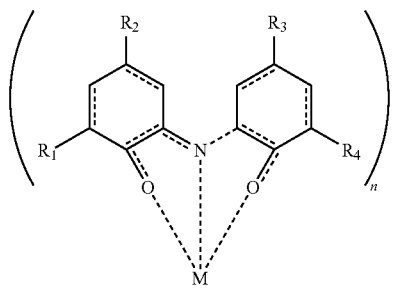

wherein:
(a) $R_1$, $R_2$, $R_3$ and $R_4$ are independently selected from the group consisting of: alkyl, branched alkyl, cycloalkyl, aryl, substituted aryl, heteroaryl, alkoxy, halogen, dialkylamino, polyoxyalkylene, carboxyl, acyl, and hydrogen; and
(b) n is from about 1 to about 4; and
(c) M is Si.

2. A compound, said compound comprising:

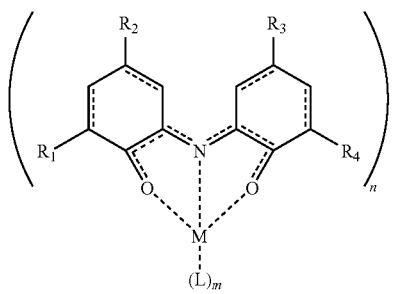

wherein:
(a) $R_1$, $R_2$, $R_3$ and $R_4$ are independently selected from the group consisting of: alkyl, branched alkyl, cycloalkyl, aryl, substituted aryl, heteroaryl, alkoxy, halogen, dialkylamino, polyoxyalkylene, carboxyl, acyl, and hydrogen; and
(b) n is from about 1 to about 4, and L comprises a ligand; m is from about 1 to about 4;
(c) M is Si.

3. A thermoplastic composition comprising a radiation absorbing compound, said radiation absorbing compound comprising:

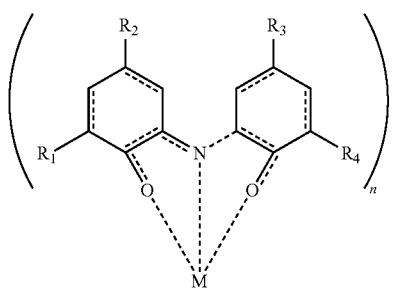

wherein:
(a) $R_1$, $R_2$, $R_3$ and $R_4$ are independently selected from the group consisting of: alkyl, branched alkyl, cycloalkyl, aryl, substituted aryl, heteroaryl, alkoxy, halogen, dialkylamino, polyoxyalkylene, carboxyl, acyl, and hydrogen;
(b) n is from about 1 to about 4; and
(c) M is Si.

4. A thermoplastic composition comprising a radiation absorbing compound, said radiation absorbing compound comprising:

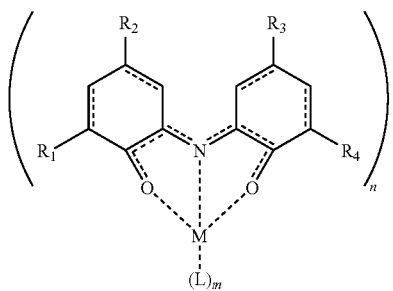

wherein:
(a) $R_1$, $R_2$, $R_3$ and $R_4$ are independently selected from the group consisting of: alkyl, branched alkyl, cycloalkyl, aryl, substituted aryl, heteroaryl, alkoxy, halogen, dialkylamino, polyoxyalkylene, carboxyl, acyl, and hydrogen; and
(b) n is from about 1 to about 4;
(c) said M is Si; and
(d) said L comprises a ligand, and m is from about 1 to about 4.

5. The thermoplastic composition of claim 4 wherein said ligand L is selected from the group consisting of at least one of the following: alkyl, alkene, allyl, alkynyl, pyridine, bipyridine, terpyridine, chloride or other halogens, perchlorate, sulfate, phosphate, organophosphate, phosphines, cyclopentadienyl, acetate, malonate, alkanoate, benzoates, acetylacetonate, alkoxide, oxide, Schiff bases, amines, imines, thiols, diamines, thiolenes, indoanilines, azos, formazyls, phthalocyanines, phenyl, substituted phenyl, merocyanines, carbonyl, cyano, oxo, carboxyl, aqua, hydroxo, sulfato, sulfito, nitrito, nitro, nitrosyl, isothiocyanato, thiosulfato, ethylene diamine, oxalato, ethylene diamine tetraacetic acid, cabonato, amido, imido, nitrido, ammino, peroxo, phosphato, phosphito, phosphido, borato, sulfido, porphyrin, monoximes, crown ethers, cryptates, chromato, chromito, hydrido, cyclypentyldieno, aryls, polyoxyalkylene, siloxanes, thiacyls, and one repeat unit or side chain of a larger polymer.

* * * * *